United States Patent
Yogev et al.

(10) Patent No.: US 8,366,966 B2
(45) Date of Patent: Feb. 5, 2013

(54) METHODS AND SYSTEMS FOR PRODUCING ENERGY FROM CARBON DIOXIDE

(75) Inventors: Amnon Yogev, Rechovot (IL); Eliyahu Gamzon, Moshav Beit Oved Doar-Na Nahal Soreq (IL)

(73) Assignee: Engineuity Research and Development Ltd., Yavne (IL)

( * ) Notice: Subject to any disclaimer, the term of this patent is extended or adjusted under 35 U.S.C. 154(b) by 652 days.

(21) Appl. No.: 11/818,967

(22) Filed: Jul. 13, 2007

(65) Prior Publication Data

US 2012/0178832 A1     Jul. 12, 2012

Related U.S. Application Data

(60) Provisional application No. 60/862,827, filed on Oct. 25, 2006.

(51) Int. Cl.
*B01J 19/00* (2006.01)
*H01M 8/06* (2006.01)

(52) U.S. Cl. .................. 252/373; 423/657; 518/704
(58) Field of Classification Search .................. None
See application file for complete search history.

(56) References Cited

U.S. PATENT DOCUMENTS

| | | | |
|---|---|---|---|
| 3,442,620 A * | 5/1969 | Schora, Jr. et al. | 423/658 |
| 3,630,669 A * | 12/1971 | Naito et al. | 423/101 |
| 3,648,668 A | 3/1972 | Pacheco | |
| 4,112,050 A * | 9/1978 | Sartori et al. | 423/223 |
| 4,126,668 A | 11/1978 | Erickson | |
| 4,132,764 A | 1/1979 | Cines et al. | |
| 4,172,924 A * | 10/1979 | Warszawski | 429/15 |
| 4,310,503 A * | 1/1982 | Erickson | 423/657 |
| 4,497,637 A | 2/1985 | Purdy et al. | |
| 4,564,595 A | 1/1986 | Neves | |
| 4,702,894 A | 10/1987 | Cornish | |
| 4,836,184 A | 6/1989 | Senne | |
| 5,143,047 A | 9/1992 | Lee | |
| 6,454,944 B1 | 9/2002 | Raven | |
| 6,696,501 B2 * | 2/2004 | Schanke et al. | 518/705 |
| 2004/0025715 A1 | 2/2004 | Bonde et al. | |
| 2005/0042166 A1 | 2/2005 | Kindig et al. | |
| 2006/0024801 A1 | 2/2006 | Holtzapple et al. | |
| 2006/0222585 A1 | 10/2006 | Verser et al. | |

(Continued)

FOREIGN PATENT DOCUMENTS

GB     638769 A        6/1950
JP     03-231199       10/1991

(Continued)

OTHER PUBLICATIONS

International Search Report, mailed Jan. 26, 2009, from corresponding International Application No. PCT/IL2007/001576.

(Continued)

*Primary Examiner* — Melvin C Mayes
*Assistant Examiner* — Colin W Slifka
(74) *Attorney, Agent, or Firm* — Pearl Cohen Zedek Latzer, LLP

(57) ABSTRACT

A method and system for producing a liquid fuel comprising:
(a) reacting water with a first metal in a first reaction chamber to obtain hydrogen, heat, and an oxide of the first metal;
(b) reacting carbon dioxide with a second metal, which is the same or different from the first metal, in a second reaction chamber, which is the same or different from the first reaction chamber, to obtain carbon monoxide, heat, and oxide of the second metal;
(c) regenerating said first and second metals from said first and second oxides.

10 Claims, 6 Drawing Sheets

U.S. PATENT DOCUMENTS

| | | |
|---|---|---|
| 2007/0001462 A1 | 1/2007 | McNeil |
| 2007/0029264 A1 | 2/2007 | Bowe |
| 2007/0129450 A1 | 6/2007 | Barnicki et al. |

FOREIGN PATENT DOCUMENTS

| | | |
|---|---|---|
| WO | 2006/006164 | 1/2006 |
| WO | 2006031757 A1 | 3/2006 |
| WO | WO 2006/123330 | 11/2006 |

OTHER PUBLICATIONS

Olah, G. A., "Beyond Oil and Gas: The Methanol Economy," Angewandte Chemie International Edition, vol. 44(18), 2005, 2636-2639, abstract only.

Weimer, T. et al., "Methanol from atmospheric carbon dioxide: a liquid zero emission fuel for the future," Energy Conversion and Management, vol. 37, Nos. 6-8, 1996, 1351-1356.

Dellepiane Daniela et al.: "clean energy from sugarcane waste: feasibility study of an innovative application of bagasse and barbojo" 2003, J of Power Sources vol. 122, pp. 47, 48, 49, ISSN: 0378-7753.

International Search Report and Written Opinion issued on Dec. 30, 2008 for PCT/IL2008/000964.

Office Action issued for U.S. Appl. No. 12/668,051 on Aug. 23, 2011.

Office Action issued for U.S. Appl. No. 12/668,051 on Mar. 2, 2012.

Extended Search Report issued for EP patent application No. 08763703.9 on Mar. 29, 2012.

Ebrahim et al.: "Kinetic Study of Zinc Oxide Reduction by Methane", Trans ICHEME, vol. 79, 2001, pp. 62-70, XP022535763.

Ebrahim et al.: "Synthesis Gas Production by Zinc Oxide Reaction with Methane: Elimination of Greenhouse Gas Emission from a Metallurgical Plant", Energy Conversion and Management, vol. 45, 2004, pp. 345-363 XP004463907.

Ao et al.: "Novel Method for Metallic Zinc and Synthesis Gas Production in Alkali Molten Carbonates", Energy Conversion and Management, vol. 49, Apr. 14, 2008, pp. 2063-2068, XP022694938.

Ao et al.: "Comparative Study on the Reaction of Methane over a ZnO Bed in the Absence and Presence of CO2", Journal of Natural Gas Chemistry, vol. 17, Mar. 2008, pp. 81-86 XP022936792.

Office Action issued for EP patent application No. 07849602.3 on Oct. 23, 2009.

Office Action issued for EP patent application No. 07849602.3 on Aug. 25, 2010.

Office Action issued for EP patent application No. 07849602.3 on Nov. 11, 2011.

"Biogas Production from maize and clover grass estimated with the methane energy value system", engineering the Future, Sep. 12-16, 2044, Leuven, Belgium, and International Water Association: 10th world congress—anaerobic digestion, Aug. 29-Sep. 2, 2004, Montreal Canada.

* cited by examiner

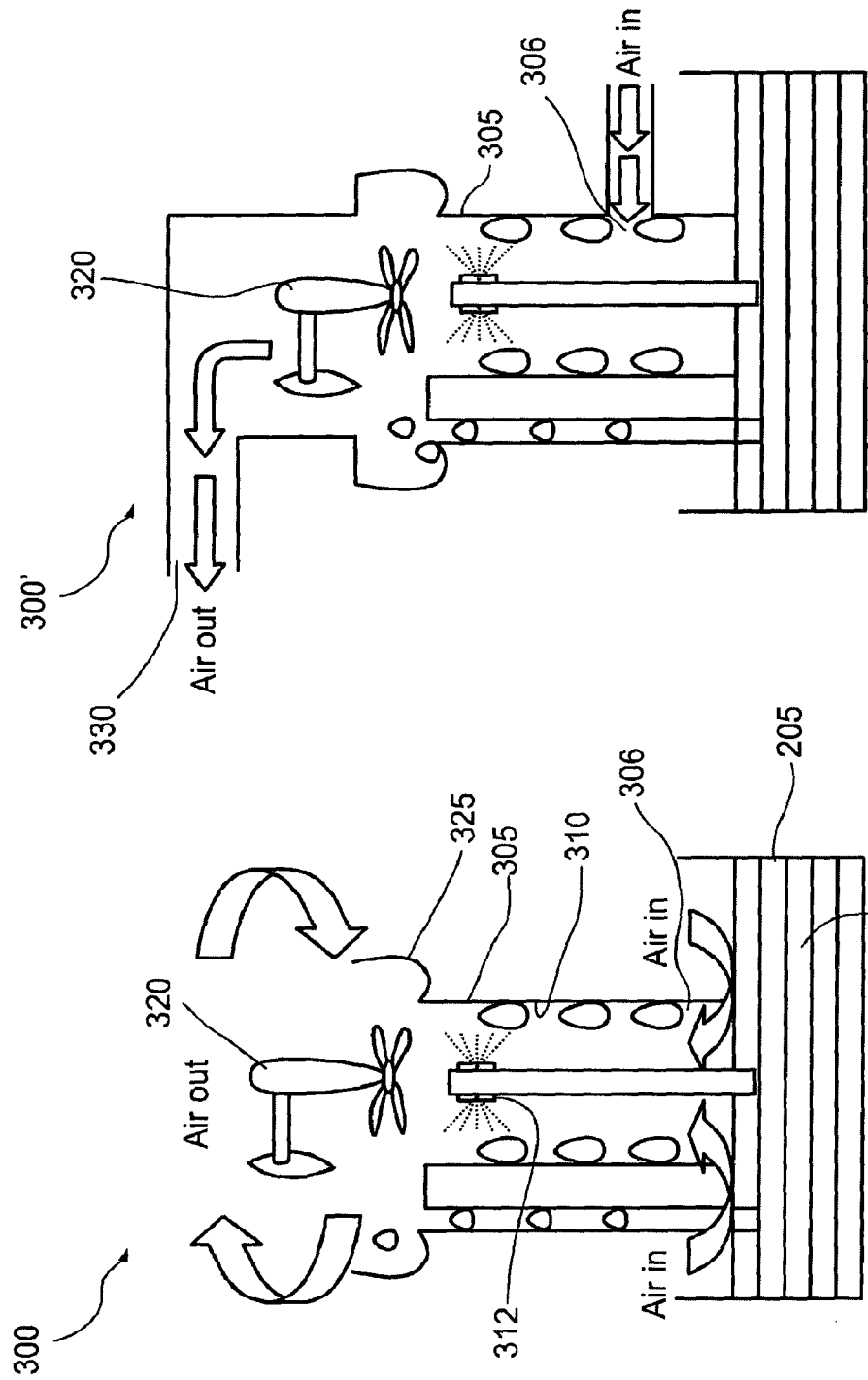

METHODS AND SYSTEMS FOR PRODUCING ENERGY FROM CARBON DIOXIDE

FIELD OF THE INVENTION

The present invention relates to methods for producing methanol or other fuels from simpler molecules, such as carbon dioxide, water, and/or methane. The invention also relates to apparatuses for carrying out such methods.

BACKGROUND OF THE INVENTION

In view of the high prices of gasoline, and the environmental problems associated with its wide use, it is desirable to develop an energy carrier that would replace, at least partially, the use of gasoline and reduce $CO_2$ emission.

One such alternative energy carrier is methanol. A hypothetical future economy based on the idea of using methanol instead of fossil fuels as a means of transportation of energy is sometimes termed "the methanol economy". The article *Beyond Oil and Gas: The Methanol Economy* authored by George A. Olah and published in Angewandte Chemie International Edition Volume 44, Issue 18, Pages 2636-2639, 2005, advocates the methanol economy and discusses the generation of methanol from carbon dioxide or methane.

SUMMARY OF THE INVENTION

An aspect of some embodiments of the invention relates to making fuel that is friendly to the environment, and preferably by consuming greenhouse gases, such as carbon dioxide and methane.

In exemplary embodiments of the invention, the greenhouse gases are taken from the atmosphere, or from processes that release them to the atmosphere.

An aspect of some embodiments of the invention relates to making fuel, for instance, methanol, from carbon dioxide ($CO_2$) and water by reacting them with a metal.

As a by-product, metal oxide is obtained. In preferred embodiments of the invention, the metal is regenerated from the metal oxide. Optionally, the metal is regenerated by electrolysis of the metal oxide. Additionally or alternatively, at least part of the metal is regenerated by reacting the metal oxide with methane, or any other carbonaceous material.

In an exemplary embodiment of the invention, air is used as a source of $CO_2$.

In another exemplary embodiment of the invention, $CO_2$ is obtained from processes that produce it as a side-product, for instance, in processes that produce fuel from biological sources, for instance, corn fermentation.

In another exemplary embodiment of the invention, $CO_2$ is obtained from landfills or natural gas sources, where it is naturally present together with methane ($CH_4$). In this embodiment, $CO_2$, water, methane and the metal are reacted together to produce syngas and metal oxide. Without being bound to theory, it is assumed that the $CO_2$ react with the metal to produce CO and metal oxide; water reacts with the metal to produce hydrogen and metal oxide, and the methane reacts with the metal oxide to obtain more CO and metal. This way, some of the metal consumed by the water and the $CO_2$ is regenerated by the methane, and the amount of metal oxide that has to be regenerated by electrolysis, is smaller than would be without the methane. In an exemplary embodiment of the invention, presence of methane in the process saves about two thirds of the electricity required for regenerating the metal from the metal oxide.

Optionally, a process and/or system according to the invention may be used for storing electrical energy. Many conventional power plants produce at off-peak hours, for instance at night and during week ends more electrical energy that the consumers consume. There is a need in the art to store such electrical energy, in a way that allows its use in the peak-usage hours. In an exemplary embodiment of the invention, metal is regenerated from the produced metal oxide by electrolysis at off-peak hours, using cheep electricity, and the produced metal is used to produce methanol to replace expensive electricity at peak-usage times. Alternatively or additionally, methanol is produced in off-peak hours, and used in peak hours to produce electricity, for instance, using a gas turbine.

An embodiment of the invention provides an apparatus for producing fuel from atmospheric $CO_2$ as a stand-alone fuel production appliance, which consumes $CO_2$ from the air, water from any available source, and energy. Optionally, energy is obtained from renewable sources, such as solar power, wind energy, hydro energy, or the like. Alternatively or additionally, energy is obtained from conventional carbon based electric power sources.

In an exemplary embodiment of the invention, a fuel producing apparatus comprises the following units:

I—A carbon dioxide separation unit—this unit captures $CO_2$ from the air, or from any other available source, and releases the $CO_2$ for use in unit II described below. Optionally, this unit consumes only air and heat.

II—A syngas producing unit—this unit consumes water and the $CO_2$ provided by the first unit, and possibly also methane or any other carbonaceous material; and reacts them with a metal to produce hydrogen and carbon monoxide (CO), the mixture thereof is known in the art as synthesis gas, or in short, syngas. This unit produces excess heat and creates a metal oxide as waste. Optionally, the excess heat is used in unit I, and the waste metal oxide is turned into metal in unit IV.

III—A fuel producing unit—this unit produces carbonaceous fuel, for instance, methanol, from the syngas produced by the syngas producing unit.

IV—an optional metal regenerating unit, for regenerating the metal from the metal oxide produced in the syngas producing unit. The metal recycling unit may reduce considerably the metal consumption of the entire apparatus, and in some cases reduce this consumption to zero.

Optionally, the metal recycling unit comprises an electrolysis bath, configured to electrolyze the metal oxide to produce the metal.

In exemplary embodiments of the invention, hydrogen produced by the electrolysis of the metal oxide is added to the fuel producing unit, thus saving at least a portion of the metal and the electricity required for recycling this portion of metal. Other hydrogen sources may also be used for supplying hydrogen to the fuel producing unit, in addition, or instead of, reacting water with the metal.

Alternatively or additionally, the metal recycling unit comprises a reaction chamber for reacting the metal oxide with methane or other low grade carbonaceous material as to regenerate the metal. Optionally, such metal recycling unit receives heat from a heat source, for instance, a solar heat source, and/or heat from the syngas producing unit.

Alternatively or additionally, metal recycling may be accomplished by heating the metal oxide to sufficiently high temperatures. Heat for such recycling process may be obtained, for instance, from solar energy.

Electric power may be supplied to the various units I-IV from any available power source, such as national or regional power plant. Alternatively or additionally, the apparatus includes a fifth unit (hereinafter unit V), which produces electric power for operating the other units from locally available renewable sources such as wind or solar energy.

Thus, in accordance with an exemplary embodiment of the invention, there is provided a method comprising:

(a) reacting water with a first metal in a first reaction chamber to obtain hydrogen, heat, and an oxide of the first metal;

(b) reacting carbon dioxide with a second metal, which is the same or different from the first metal, in a second reaction chamber, which is the same or different from the first reaction chamber, to obtain carbon monoxide, heat, and oxide of the second metal;

(c) regenerating said first and second metals from said first and second oxides.

In an exemplary embodiment of the invention, the method comprises reacting said carbon monoxide with said hydrogen to obtain a fuel. Optionally, said fuel is methanlol.

Optionally, said first and second metals are the same.

Optionally, said first and second reaction chambers are the same.

Optionally, at least one of said first or second metal is zinc.

In an exemplary embodiment of the invention, said regenerating comprises electrolysis of the metal oxide. Alternatively or additionally, said regenerating comprises reacting said metal oxide with a carbonaceous material, for example, mathane.

Optionally, (a) and (b) are carried out under conditions that ensure producing hydrogen and carbon monoxide in molar ratios suitable for preparing a fuel from the obtained syngas.

In an exemplary embodiment of the invention, water, carbon dioxide, and a carbonaceous material are reacted in a same first reaction chamber. Optionally, said carbonaceous material is methane.

In accordance with an exemplary embodiment of the invention, a method as described in any of the options detailed above comprises separating $CO_2$ from a gas mixture, and introducing the separated $CO_2$ into said second reaction chamber.

Optionally, said gas mixture is air.

Optionally, separating $CO_2$ from said gas mixture comprises:

(a) contacting said gas mixture with a solution comprising water and a base to obtain a salt; and (b) heating said salt to release $CO_2$.

In an exemplary embodiment of the invention, said base comprises an alkali metal salt of an anion selected from carbonates, phosphates, polyphosphates, silicates, and borax. Optionally said base comprises $K_2CO_3$. Alternatively or additionally, said base comprises $K_3PO_4$.

In exemplary embodiments of the invention, said base is inorganic. Optionally, said inorganic base is water soluble. Optionally, said inorganic base forms with carbon dioxide a water-soluble salt, for example, $CaCO_3$. Alternatively, said inorganic base forms with carbon dioxide a water-insoluble salt.

In an exemplary embodiment of the invention, said basic solution forms with said $CO_2$ particles, optionally nanometric particles, of a water insoluble salt, said particles, being suspended in water.

In an exemplary embodiment of the invention, contacting said gas mixture with a solution comprises blowing said gas mixture above a surface of a solution reservoir containing said solution. Alternatively or additionally, contacting comprises sprinkling droplets of said solution into said gas mixture.

In an exemplary embodiment of the invention, said solution also contains a surface active agent, which reduces surface tension of said solution.

Additionally or alternatively, said solution comprises a water soluble substance, which reduces the partial vapor pressure of water and does not react with the carbon dioxide.

In an exemplary embodiment of the invention, heating the salt comprises heating water, in which the salt is dissolved and/or with which the salt is mixed, and said water soluble substance is present in such quantities, that heating the salt to release the $CO_2$ results in evaporating two mols of water with each mol of released $CO_2$. Optionally, heating the salt comprises heating with heat generated in at least one of said first or second reaction chamber.

In an exemplary embodiment of the invention, a method as described above comprises liquefying metal in a first chamber to obtain liquefied metal, and supplying the liquefied metal into said first and/or second reaction chambers.

Optionally, liquefying is with heat produced in said first and/or second reaction chamber. Optionally, supplying the liquefied metal is via a sprinkler or a nozzle.

In an exemplary embodiment of the invention, regenerating said first and second metals from said first and second oxides comprises collecting said oxides, cooling said oxides, and reacting said cooled oxides as to form said first and second metals.

Optionally, such an embodiment comprises dissolving said oxides in an acid. Preferably, said dissolving is after said cooling and before said reacting. Optionally, reacting said cooled oxides comprises applying electrolysis to the dissolved oxides.

In accordance with an exemplary embodiment of the invention, regenerating said first and second metals from said first and second oxides comprises collecting said oxides, and reacting said oxides as to form said first and second metals, wherein said reacting comprises decomposing said oxides by heat, optionally, said heat is from a solar heat source.

In an exemplary embodiment of the invention, least one of reacting said first metal or reacting said second metal comprises supplying a metal to a metal container in solid state, liquefying the metal to obtain liquefied metal, and introducing said liquefied metal into at least one of said first or second reaction chambers. Optionally, said metal in solid state comprises a rod or wire of said metal.

There is further provided in accordance with an exemplary embodiment of the invention, a method of separating $CO_2$ from air, the method comprising:

(a) contacting said air with a solution comprising water and a base to obtain salt in said water; and (b) heating said salt to release $CO_2$, wherein said solution contains a surface active agent, which reduces surface tension of said solution.

Optionally, said gas mixture is air.

Optionally, contacting comprises sprinkling droplets of said solution.

Optionally, said solution comprises a water soluble substance, which reduces the partial vapor pressure of the water and does not form a salt with carbon dioxide.

In an embodiment of the invention, heating the salt comprises heating the water, and said water soluble substance is present in such quantities, that heating the salt to release the $CO_2$ results in evaporating two mols of water with each mol of released $CO_2$.

In an exemplary embodiment of the invention, contacting the gas mixture with a solution comprises bubbling said gas mixture into said solution.

Optionally, contacting the gas mixture with a solution comprises flowing said gas mixture into a tower having an inner wall, and sprinkling said solution towards said inner wall. Optionally, said flowing is through a gas inlet that is configured to receive wind and follow the direction of the wind. Optionally, said flowing comprises operating a fan, and said fan also pushes water droplets radially to return them to said water reservoir. Optionally, said tower comprises internal structures, for example, granular particles, enlarging a surface available for contacting said gas mixture with said solution.

In an exemplary embodiment of the invention, said contacting comprises spraying said solution into a flow of said gas mixture. Optionally, said spraying is downwards, as to be facilitated by gravity.

In accordance with embodiments of the invention according to any of the previously mentioned options, the method comprises cooling said syngas before producing fuel therefrom. Optionally, said cooling comprises operating a gas turbine with the syngas as a working fluid.

It is further provided in accordance with an exemplary embodiment of the invention, a system for producing liquid fuel comprising:

(a) A syngas producing unit, configured to receive $CO_2$ and water, and reacting said $CO_2$ with a first metal and said water with a second metal, which is the same or different from said first metal, to produce hydrogen and carbon monoxide;

(b) a fuel producing unit, configured for producing a carbonaceous fuel from products of the syngas producing unit; and (c) a metal regenerating unit, configured for regenerating metal from metal oxide produced in the syngas producing unit.

Optionally, said system comprising a carbon dioxide separation unit, configured to capture $CO_2$ from a gas mixture, releasing said $CO_2$, and transferring said $CO_2$ to said syngas producing unit.

Optionally, said system comprising an electric power producing unit, configured to produce electric power from renewable sources.

In an exemplary embodiment of the invention, said syngas producing unit comprises:

(a) a container with liquid metal, (b) a reaction chamber, configured for receiving liquid metal from said container and at least one of water and $CO_2$, and having a gas inlet, configured for letting out syngas produced in the reaction chamber; and (c) a heat transferring member for transferring heat from said reaction chamber to said container.

Optionally, said container with liquid metal has a metal inlet, for introducing metal in solid state into said container. Optionally, said inlet comprises elastic seals.

Optionally, said heat transferring member is a portion of said container, said portion directly contacting liquid metal in said container.

Optionally, said reaction chamber and said container are concentric. Optionally, a system as described in any of the options above comprises a heat transfer member for transferring heat from said reaction chamber to said $CO_2$ separation unit.

Optionally, said metal regenerating unit comprises an electrolytic bath.

Optionally, said reaction chamber is configured for receiving a carbonaceous material, for example, methane, and reacting said carbonaceous material with a metal oxide produced by a reaction between said metal and said water and/or said $CO_2$.

Optionally, said first and second metal are the same.

Optionally, said metal regeneration unit comprises:

a conduit, for receiving metal oxide from said syngas producing unit and transferring said metal oxide to a metal reproducing unit;

a heat exchanger, for cooling said metal oxide;

a first valve and a second valve defining between them along said conduit an intermediate zone, said first valve connecting said intermediate zone to said syngas producing unit and said second valve connecting said intermediate zone to said metal reproducing unit. Optionally, the system comprises an acid inlet for introducing an acid into said intermediate zone.

Optionally, said metal reproducing unit comprises an electrolytic bath.

Optionally, said reproducing unit comprises a solar heater, capable of heating said metal oxide as to decompose it.

Alternatively or additionally, said reproducing unit comprises an inlet for a carbonaceous material.

In accordance with an exemplary embodiment of the present invention, there is provided a method comprising contacting a metal, water, carbon dioxide, and a carbonaceous material to produce a mixture comprising hydrogen and carbon monoxide. Optionally, said carbonaceous material is methane.

Optionally at least a portion of said carbon dioxide and at least a portion of said carbonaceous material originate in a landfill.

In exemplary embodiments of the invention, methods as in any of the options described above are provided, wherein at least a portion of said carbon dioxide is produced by a fermentation process. Optionally, at least a portion of said carbon dioxide and at least a portion of said methane originate in natural gas. Optionally, in such a method, a metal oxide is produced, and said metal oxide is electrolyzed to regenerate said metal. Alternatively or additionally, the method comprises heating said metal oxide to form said metal. Optionally, said heating is with heat obtained from solar energy. Optionally, said heating is in the presence of a carbonaceous material.

In an exemplary embodiment of the invention, the method comprising contacting said electrolyzed metal oxide with a metal, water, carbon dioxide, and methane to produce a mixture comprising hydrogen and carbon monoxide.

In an exemplary embodiment of the invention, a method according to any of the options described above, comprises producing electric power from said fuel at peak hours and consuming electric power only at off-peak hours.

In accordance with a still further exemplary embodiment of the invention there is provided a method of producing electricity from a landfill comprising:

producing syngas from methane and $CO_2$ originating in the landfill;

producing a fuel from said syngas and producing electrical energy from said fuel;

wherein said producing syngas and/or producing fuel utilizes electrical energy during off-peak hours, and said producing electrical energy is during peak hours. Optionally, producing syngas is according to a any of the embodiments of the invention.

BRIEF DESCRIPTION OF THE DRAWINGS

Embodiments of the invention are herein described, by way of example only, with reference to the accompanying drawings. It is stressed that the particulars shown are for purposes of illustrative discussion of the described embodiments, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice.

In the drawings:

FIGS. 3A and 3B are schematic illustrations of units for capturing $CO_2$ from air according to exemplary embodiments of the invention;

DETAILED DESCRIPTION OF EXEMPLARY EMBODIMENTS

Figure 1A:
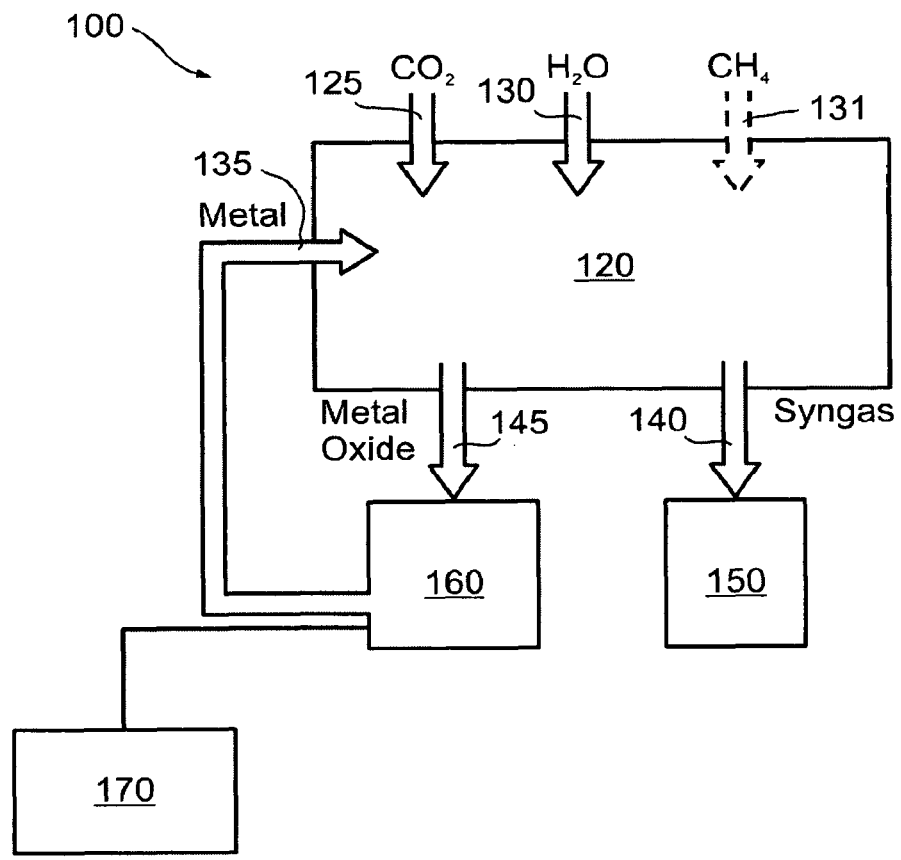
FIG. 1A is a simplified block diagram of a system for producing syngas according to an embodiment of the invention.

In the following, some general features of exemplary embodiments of the invention are first outlined, and then, exemplary embodiments are described in detail.

Separating Carbon Dioxide

One aspect of some embodiments of the invention concerns a device and a method for capturing $CO_2$ from the air. Optionally, $CO_2$ (which is an acidic entity) is captured with a basic solution contacting the air. A similar approach is optionally used for separating $CO_2$ from other mixtures of gases.

Preferably, the basic solution is basic due to presence of a selected inorganic base. Inorganic bases are usually more stable than organic bases, and have smaller tendency to decompose.

Preferably, the selected inorganic base forms with $CO_2$ a buffer solution, such that the pH of the solution is insensitive to the amounts of $CO_2$ absorbed. In this sense, bases capable of reacting with more than one $CO_2$ molecules per base molecule, are preferred.

Optionally, the selected inorganic base is water soluble, and forms with the captured $CO_2$ a water soluble salt. In this context, "water soluble" means that under working conditions, all the salt is dissolved in the water. Examples of such bases include alkali salts of anions of the following families: carbonates (for instance, $K_2CO_3$), phosphates (for instance, $K_3PO_4$), polyphosphates, silicates, and/or borax.

Optionally, the inorganic base forms with the $CO_2$ a water insoluble salt (For instance $CaCO_3$). Preferably, the insoluble salt is obtained from the basic solution and the $CO_2$ in the form of suspension. of the salt, rather than a solution.

Contacting the Basic Solution with the Air

In an embodiment of the invention, the basic solution is sprinkled from a tower, for instance, 10 m high, and the sprinkled solution absorbs $CO_2$ from the air on its way down. Optionally, the air is streamed in perpendicular to the direction of the water.

In another embodiment of the invention, air is bubbled into the basic solution. Preferably, bubbling is combined with stirring. Optionally, stirring comprises bubbling air into the solution at one or more off-center positions. Preferably, bubbling is in shallow pools, or in deep pools close to their upper surface, such that the bubbles are not formed against high pressure formed by the weight of the solution above them. Using bubbling reduces and in some cases obviates the use of surface active agents.

In an embodiment of the invention, air is sucked (or pushed) either up or down a tower and the basic solution is sprinkled inside the tower, preferably on the walls of the tower, to create a two phase counter-flow.

Optionally, air sucked (or pushed) to the end of the tower, together with solution sprinkled into the tower and carried along with the air are centrifuged as to separate the solution from the air, and collect the solution for separation of $CO_2$ and reuse of the solution. Optionally, sucking the air is by a fan. Optionally, centrifuging the solution and air is by the same fan, which sucks the air up the tower and pushes the solution reaching it in a radial direction.

Improving $CO_2$ Absorption of the Basic Solution

In embodiments where contacting the basic solution with the air comprises supplying the solution in droplet form, for instance, when sprinkling is used, it is preferred to reduce the surface tension of the drops, since this surface tension creates an inner pressure working against absorption of $CO_2$.

Optionally, reducing the surface tension of the droplets is performed by including a surface active agent in the solution to reduce the surface tension.

Optionally, the surface active agent is itself basic, and may replace at least a portion of the base in the basic solution.

Figure 1B:
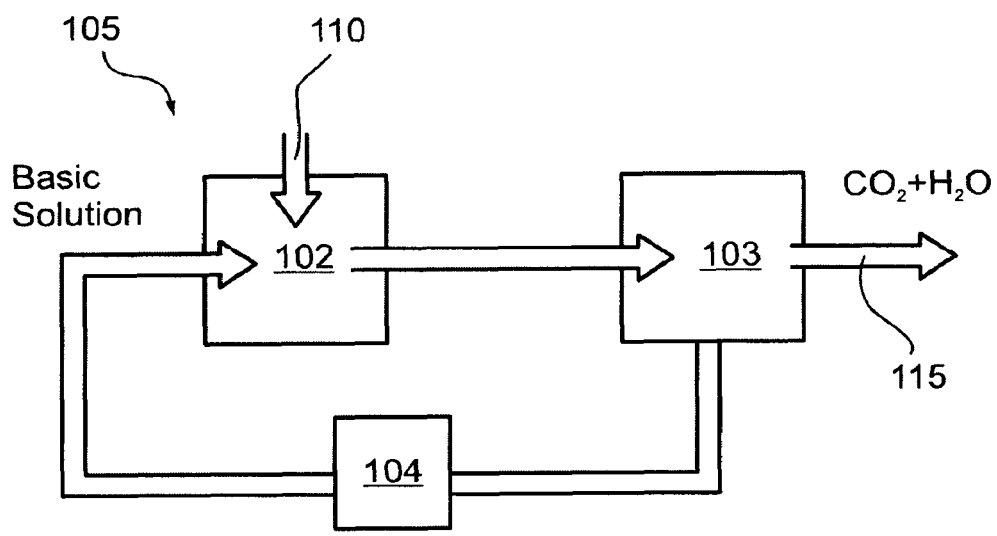
FIG. 1B is a simplified block diagram of a unit for separating $CO_2$ from a gas mixture according to an exemplary embodiment of the invention.

Preferably, the surface active agent is of a kind that is operable at the high temperatures at heating zone 103 (see FIG. 1B). This temperature depends on the base used to capture the $CO_2$, and may be easily determined by those skilled in the art from readily available thermodynamic equations and data.

Non-limiting examples for suitable surface active agents include alkali salts of phosphates (for instance, $K_3PO_4$), polyphosphates, silicates, calcium hydroxide, and borax.

Releasing $CO_2$ from the Solution

In an exemplary embodiment of the invention, releasing $CO_2$ from the basic solution comprises heating the solution to a selected temperature. This heating optionally evaporates water from the solution, and the evaporated water may be used together with the released $CO_2$ to generate syngas. The pressure is preferably adjusted to allow heating the solution to the selected temperature. Pressure and temperature values used for releasing the $CO_2$ from the salt are optionally selected as to obtain $CO_2$ and water in desirable ratio.

Additionally or alternatively, the ratio between $CO_2$ and water vapor obtained in the heating is controlled by adding to the solution a water soluble substance, which reduces the molar ratio of the water in the basic solution. An example of a suitable water soluble substance is potassium fluoride (KF). Optionally, the water soluble substance and its quantity are selected to evaporate just enough water to allow quantitative reaction between the water and the $CO_2$ to give the required fuel. For instance, if methanol is to be produced, a preferred water: $CO_2$ ratio is 2:1. An alternative option is to evaporate more water than is required for the reaction, condense the water excess, and return the water to the $CO_2$ capturing unit.

Alternatively or additionally, the reaction may be carried out at excess of $CO_2$ over water. In some embodiments, this broadens the temperature range at which the syngas production reaction is feasible.

Conditions for Producing Syngas from Water and Carbon Dioxide

A reaction of metal with water provides hydrogen (and metal oxide); a reaction of metal with $CO_2$ provides CO (and metal oxide), and the mixture of hydrogen and CO is syngas.

Producing syngas from $CO_2$ and water is done in accordance with some embodiments of the invention by reacting $CO_2$ and water with a metal. In an exemplary embodiment of the invention, water and $CO_2$ are reacted with the metal in a single reaction chamber. Alternatively, water is reacted with a metal at one reaction chamber, and $CO_2$ is reacted with a metal in another reaction chamber. Optionally, water and $CO_2$ are introduced into the syngas producing unit in a proportion such that the resultant CO and hydrogen are in quantities suitable for producing methanol, e.g., in molar ratio of 1 CO:2 $H_2$.

Generally, these conditions comprise temperature of about 200° C. and pressure of about 50 Atmospheres (5000 kPa). Thus, in a preferred embodiment of the invention, water and $CO_2$ are reacted with a metal to obtain hydrogen and CO at about 50 Atm. In an exemplary embodiment, syngas is produced at about 800° C. and cooled to about 200° C. before it is introduced into the fuel producing unit.

Conditions for Producing Syngas from Water, Carbon Dioxide, and Methane

In some embodiments of the invention, methane or any other carbonaceous material is also introduced into the syngas producing unit. In such embodiments, it is optional to operate the unit with carbon dioxide: methane: water molar ratios of 1:1:2, which leaves no excess of either of the reactants. Here also, preferable working temperature is around 800° C., and excess of carbon sources over the hydrogen source, allows working at a broader temperature range.

As the reaction between methane and metal oxide is endothermic, in some embodiments it consumes the heat produced by the exothermic reactions of water and/or carbon dioxide with the metal, and lowers the temperature in the syngas producing unit to below preferable operation temperature. In these embodiments, it may be advisable to supply the syngas producing unit with heat from an external source, for example, from the fuel-producing unit.

Syngas Producing Reactions

Preferably, metal is introduced into the reaction chamber in small droplets, to let the gases react with the metal faster. Introducing the metal as droplets may be with any commercially available metal sprayer, as, for instance, those used for spraying corrosion-resistant coatings, such as zinc or aluminum.

The metals are preferably but not limited to Al, Mg, and Zn, or alloys of these metals or alloys of one or more of these metals with other metals.

In some embodiments, metal oxide produced in the reaction chamber sinks on the floor of the reaction chamber due to its relatively high density. This metal oxide is optionally removed from the reaction chamber through an outlet in the floor of the reaction chamber.

Optionally, the removed metal oxide is then cooled, and reacted with an acid to provide an aqueous solution. Optionally, the produced aqueous solution is electrolyzed to obtain metal that is optionally used again to react with fresh water and $CO_2$.

In some embodiments, part or all of the metal oxide is created as a powder made of very small particles, and rather than sinking to the floor of the reaction chamber, this powder floats and creates together with the produced gas an aerosol. In this embodiment, the metal oxide is removed from the reaction chamber together with the produced gases. In an embodiment of the invention, the produced aerosol is cooled, and bubbled into an electrolysis solution, in which the metal oxide reacts to produce metal and the gases contained in the aerosol leave the electrolysis solution free of metal oxide powder.

Heat Economy

In a preferred embodiment of the invention, heat produced in one or more of the exothermic (heat producing) processes is supplied to the endothermic (heat consuming) processes.

As described above, the heat endothermic processes optionally include releasing the $CO_2$ from the solution, and the exothermic processes optionally include:

Condensing steam that evaporated from the solution when the $CO_2$ was released;
Reacting a metal with water, $CO_2$ and/or methane;
Cooling the metal oxide before hydrolyzing it; and
Producing fuel from syngas.

Optionally, heat produced in one or more of the exothermic processes is used to operate a heat machine, for instance, a turbine.

In an exemplary embodiment of the invention, syngas exits the syngas producing unit at about 800° is cooled or heated to a temperature selected for producing the fuel in the fuel producing unit.

Optionally, syngas exits the syngas producing unit at a pressure suitable for producing the fuel at the selected temperature.

Optionally, cooling the syngas comprises expanding it through a gas turbine, thus utilizing the heat carried by the syngas to produce work. Additionally or alternatively, heat excess from any of the units in a system according to embodiments of the invention may be used for operating one or more steam turbine(s).

In stand-alone power production appliances, it is possible to use excess heat for heating houses, water in domestic water systems, etc.

Sources of $CO_2$

In an exemplary embodiment of the invention, air serves as a $CO_2$ source.

Air has relatively low concentration of $CO_2$, and the system described herein for capturing $CO_2$ from air may also be suitable for capturing it from other sources.

Alternatively or additionally, $CO_2$ is captured from gas mixtures that are rich with $CO_2$. One example of such a gas mixture is natural gas. In many wells of natural gas, $CO_2$ is present together with the natural gas (methane). Usually, the $CO_2$ is treated as a contamination, separated from the methane, and released to the atmosphere. In accordance with an embodiment of the present invention, rather than separating $CO_2$ from methane, the two gases are reacted together, in the presence of water and a metal, to form synthesis gas, which is preferably used for producing a liquid fuel, such as methanol. The liquid fuel is advantageous over the natural gas in that it may be easily transferred; it does not leak as easily as gas does; it is biodegradable, and is less dangerous in handling.

Similarly, methane and carbon dioxide are present at landfills, but usually only the methane is used. In accordance with an embodiment of the present invention, the carbon dioxide is also used, to produce with the methane a liquid hydrocarbon, such as methanol.

Fermentation facilities, used for producing ethanol as a gasoline substitute, are another optional $CO_2$ source. Fermentation facilities produce ethanol from fermentation of biological material. In most cases, the production of ethanol by fermentation is accompanied with the production of $CO_2$. Using embodiments of the present invention to form methanol from this $CO_2$ may double the energy produced by these facilities, and save the environment from considerable amounts of $CO_2$.

Many other known processes produce carbon dioxide as a by-product, and release it to air, thus exacerbating the greenhouse effect. It is in accordance with embodiments of the present invention to use carbon dioxide from any such process, and use it to form syngas, and optionally, from the syngas, a hydrocarbon based fuel, preferably a liquid fuel.

Energy Sources

Some of the embodiments of the present invention consume energy. Optionally, this energy is obtained from renewable sources, such as solar energy, nuclear energy, hydroelectric energy, geothermic energy, and/or wind.

Additionally; heat produced in some steps of the inventive processes may be used to replace external energy source.

Some embodiments of the invention comprise producing metal from metal oxide. This is optionally done by electrolysis at night, when electricity is relatively cheap.

Reference is now made to the figures, which together with the above descriptions, illustrate preferred embodiments thereof.

FIG. 1A is a simplified block diagram of an apparatus 100 for producing syngas from air and water according to an embodiment of the invention. In the figure, block 120 is a syngas producing unit. Syngas producing unit 120 has an inlet 125, for receiving $CO_2$. Optionally, $CO_2$ is received from a carbon dioxide separation unit, for instance, unit 105 of FIG. 1B. Optionally, inlet 125 also receives water vapor from the $CO_2$ separation unit (105). Optionally, syngas producing unit 120 has a separate water inlet 130, but this may be omitted if the $CO_2$ is supplied with sufficient amounts of water. Optionally, syngas producing unit 120 has a methane inlet (131). In some embodiments, methane and $CO_2$ are coming from a single source, and then, a separate inlet for methane may be omitted. Optionally, syngas producing unit 120 has only one inlet, for receiving all the non-metallic reactants.

In embodiments where the $CO_2$ enters syngas producing unit 120 free of water, unit 120 may include two reaction chambers (not shown), one for reacting the $CO_2$ with a first metal, and the other for reacting water with a second metal, which may be the same or different from the first metal. In other cases, the $CO_2$ and the water may react in a single reaction chamber. Optionally, metal is introduced into the syngas producing unit through a metal inlet, 135.

Syngas producing unit 120 comprises a syngas outlet 140. Optionally, the syngas leaves unit 120 at a pressure, which is most suitable for producing methanol, that is, at about 50 Atm, although other pressures may be used. In some embodiments of the invention, the temperature and/or pressure is adjusted to the temperature and/or pressure required in fuel producing unit 150 after the syngas leaves unit 120.

Optionally, syngas outlet 140 supplies the syngas to a fuel producing unit 150, which produces fuel, for instance, methanol from the syngas by any method known in the art per se. Production of methanol from syngas is described, for instance in Kirk Othmer Encyclopedia of Chemical Technology published by Wiley Interscience.

Syngas unit 120 also comprises a metal oxide outlet 145, leading into a metal regeneration unit, 160.

Optionally, metal regeneration unit 160 comprises an electrolysis bath, in which the metal oxide is electrolyzed to produce a metal. Optionally, the electrolysis bath receives electrical power from power source 170. Power source 170 is optionally a national or regional power plant, and preferably, a local power source, producing power from renewable sources, such as solar energy, wind, hydroelectric power, etc.

Optionally, metal produced in regeneration unit 160 is introduced to the syngas producing unit, for instance, through inlet 135.

In a preferred embodiment of the invention, syngas producing unit 120 is independent of metal regeneration unit 160, such that syngas is produced irrespective of metal regeneration. This allows regenerating the metal only when cheep electricity supply is available, while producing syngas around the clock. Metal regeneration or fuel production may be limited, for instance, to daytime, when solar energy is available, to night time, when central power plants provide cheap electric power, or whenever there is wind that is capable of operating a wind driven power plant, all in accordance with the specific kind of power source 170 that is being used.

In operation, water reacts with a metal to form hydrogen and metal oxide and $CO_2$ reacts with a metal to form CO and metal oxide. In exemplary embodiments of the invention, these reactions may require ignition. Ignition is optionally supplied by electric spark, discharge, and/or a hot filament.

Metal is preferably introduced into syngas producing unit 120 during operation. Metal introduction is optionally synchronous with introduction of the other reactants, such that there is no excess of metal over the other reactants. Excess of metal may turn the reaction in the opposite direction, to produce $CO_2$ from CO and metal oxide. Metal is optionally introduced into the syngas producing unit by sprinkling with a metal sprayer, for instance, of the kind used for spraying metals to coat substrates.

Syngas produced by the reactions between $CO_2$, water, and metal in the syngas producing unit (120) exits into methanol producing unit 150, wherein fuel is catalytically prepared from the syngas using methods that are known in the art. Optionally, the fuel is an alcohol, such as methanol or ethanol, or any other hydrocarbon.

Metal oxide produced by the reactions that take place in the syngas producing unit exits into metal regeneration unit, 160, where it is reacted to regenerate the metal. The regenerated metal is optionally returned to syngas producing unit 120, to react with fresh amounts of water and $CO_2$.

FIG. 1B is a simplified block diagram of a unit 105 for separating $CO_2$ from a gas mixture according to an exemplary embodiment of the invention. Unit 105 has a gas inlet 110, for introducing into unit 105 air, or any other gaseous mixture, from which $CO_2$ is to be separated. Unit 105 comprises a $CO_2$ capturing unit 102 for contacting the gas mixture with a basic solution. FIGS. 2A-2E and FIGS. 3A-3B describe various embodiments of capturing unit 102. Capturing unit 102 optionally comprises a basic solution comprising a base that forms a salt with $CO_2$, which salt dissociates thermally to release the $CO_2$, preferably, under mild conditions. An example for such a basic solution is an aqueous solution of potassium carbonate ($K_2CO_3$) which forms, when reacted with $CO_2$, potassium bicarbonate ($KHCO_3$).

From $CO_2$ capturing unit 102, a solution containing the salt, for instance, $KHCO_3$, is transferred to heating zone 103. At heating zone 103 the solution is heated as to releases the $CO_2$. These conditions may be determined by those skilled in the art, for instance, from thermodynamic calculations. The $CO_2$ is released through outlet 115, optionally, into syngas producing unit 120 (see FIG. 1A). Optionally, vapors of water of the basic solution exits together with the $CO_2$ through outlet 115. Optionally, some of the water vapors are condensed and optionally further cooled and returned to capturing unit 102.

Cooler 104 optionally cools portions of the solution that do not exit through outlet 115. Alternatively or additionally, cooler 104 cools water evaporated through outlet 115 and condensed.

Optionally, heat for heating the salty solution at heating zone 103 is provided by the exothermic reactions carried out at system 100, for instance, at the syngas producing unit (120 of FIG. 1A).

In operation, carbon dioxide separation unit 105 receives a gas mixture that comprises carbon dioxide, and separates carbon dioxide from other gases. Optionally, not all the gases in the mixture are separated from the carbon dioxide. In an exemplary embodiment, separating carbon dioxide from the gas mixture comprises contacting the gas mixture with a solution containing potassium carbonate to form in the solution potassium bicarbonate, and releasing the $CO_2$ from the solution by heating the potassium bicarbonate.

Optionally, the solution that contains potassium bicarbnonate is heated to about 200° C., to release the $CO_2$. After the $CO_2$ is released, the basic solution is optionally cooled and reused to capture $CO_2$ from another batch of gas mixture.

In this embodiment, $CO_2$ is released in mixture with water vapor. Part or all of said water vapor is optionally condensed, cooled, and reused to capture $CO_2$ from another batch of gas mixture.

The carbon dioxide (and, optionally, water vapor) exits from separation unit 105 into syngas producing unit 120. Two embodiments of syngas producing units according to embodiments of the invention are described in relation to FIGS. 4A and 4B.

FIGS. 2A-3B are schematic illustrations of $CO_2$ capturing units. In the following, they are described with reference to capturing $CO_2$ from air, but they may also be used for capturing $CO_2$ from other gaseous mixtures, including mixtures having a richer $CO_2$ content than air.

Figure 2A:
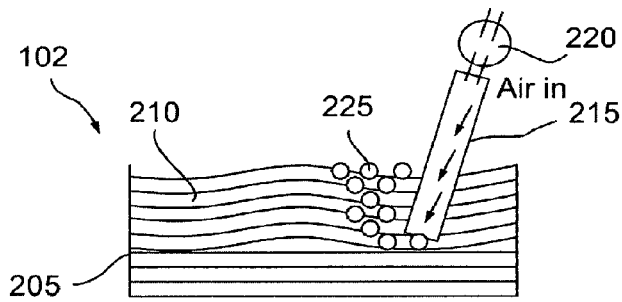
FIGS. 2A-2E are schematic illustrations of $CO_2$ capturing units according to various embodiments of the invention.

FIG. 2A is a schematic illustration of a unit 102 for capturing $CO_2$ from air according to a bubbling embodiment of the invention. A pool 205 contains a basic solution 210. Air is bubbled into basic solution 210 through a conduit 215 by a pump 220. Conduit 215 preferably releases the air at a depth of only about 10-30 cm from the upper surface of the basic solution. The air leaves the pool as bubbles 225, which are poorer in $CO_2$ than the air bubbled into the basic solution, since some of the $CO_2$ is captured in the solution.

Figure 2C:
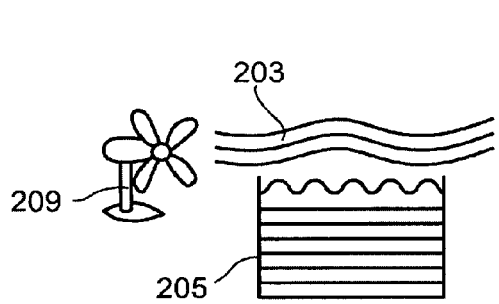
Figure 2B:
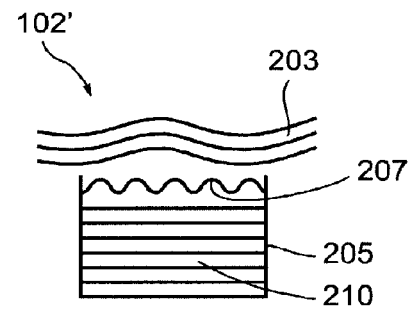

FIG. 2B is a schematic illustration of a unit 102' for capturing $CO_2$ according to an embodiment of the invention. A pool 205 forms a water reservoir containing a basic solution 210. Air 203 flows above pool 205, for instance, when the whether is windy, and creates waves 207 in the solution. The wind continues blowing away from the pool carrying with it air which is poorer in $CO_2$, since some of the $CO_2$ was captured by the solution.

FIG. 2C shows a similar embodiment, but here, air 203 is forced to flow above pool 205 by a fan 209.

Figure 2E:
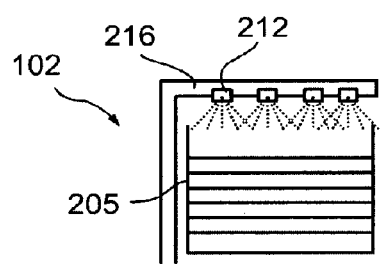
Figure 2D:
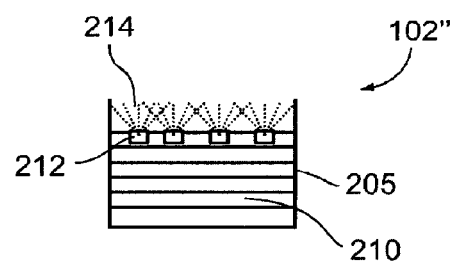

FIG. 2D is a schematic illustration of a unit 102" for capturing $CO_2$ from air according to a sprinkling embodiment of the invention. Solution 210 is sprinkled into the air through sprinklers 212. Drops 214 capture $CO_2$ from the air, and return to pool 205 by gravity. The drops are richer in $CO_2$ when they fall back then when they are sent upward. Preferably, air blows (naturally, or being forced to blow) through the spray of droplets, such that droplets 214 are sprinkled into constantly refreshed air.

FIG. 2E is a schematic illustration of a unit similar to 102", but here, sprinklers 212 are carried on a conduit 216, which is, for example, 10 m above the upper surface of the solution in pool 205. This way, the solution is sprayed downwards, which requires less energy than required for spraying the solution by the arrangement of FIG. 2D.

Optionally, a wicking system is used to contact the gaseous mixture with the basic solution. The wicking system wicks the solution from the pool up into an air flow. When the $CO_2$ is absorbed, the salt travels back down into the pool due to diffusion and gravity.

FIG. 3A is a simplified schematic illustration of $CO_2$ capturing unit 300, which is configured for capturing $CO_2$ from air according to an embodiment of the invention. Unit 300 comprises a pool 205 containing basic solution 210. Above the pool, a tower 305 is shown. Tower 305 has air inlet 306. Tower 305 has inside it sprinklers 312, which sprinkle droplets of the basic solution against the inner wall (310) of tower 305. Optionally, inner wall 310 is formed with increased surface-area. For example, inner wall 310 may be rough, have a plurality of depressions. Additionally or alternatively, the tower may be filled with particles, for instance, stones or, other internal structures, to enlarge its surface area.

At the head of tower 305, there is a fan 320, for sucking air into the tower through inlet 306. In operation, the air flows up along tower wall 310, and thus contacts water that drips along inner wall 310 back into pool 205.

Optionally, at the upper side of tower 305 there is a crown 325. Water droplets that are carried with the air up towards fan 320 are blown radially from the fan, caught in crown 325, and drip back into pool 205.

FIG. 3B is a simplified schematic illustration of a $CO_2$ capturing unit (300'), which is similar to unit 300, but provided with air inlet 306 which is configured to receive therein wind, as to save at least some of the energy required for operating fan 320.

Additionally, unit 300' is equipped with an air outlet 330, positioned opposite to air inlet 306.

Air inlet 306 is preferably configured to follow the wind. For instance, air inlet 306 may be an opening in a ring that rotates around the longitudinal axis of tower 305, such that the opening constantly faces the wind.

Figure 4A:
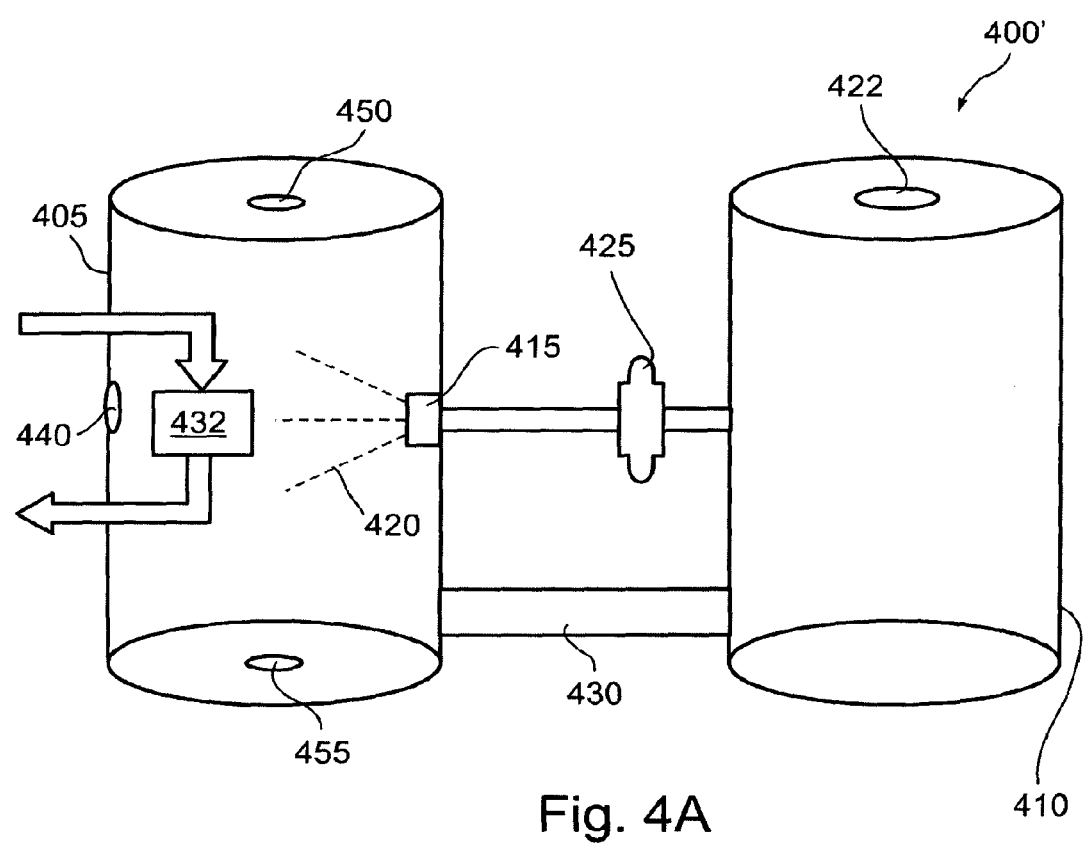
FIGS. 4A and 4B are schematic illustrations of syngas producing units according to embodiments of the invention.
Figure 4B:
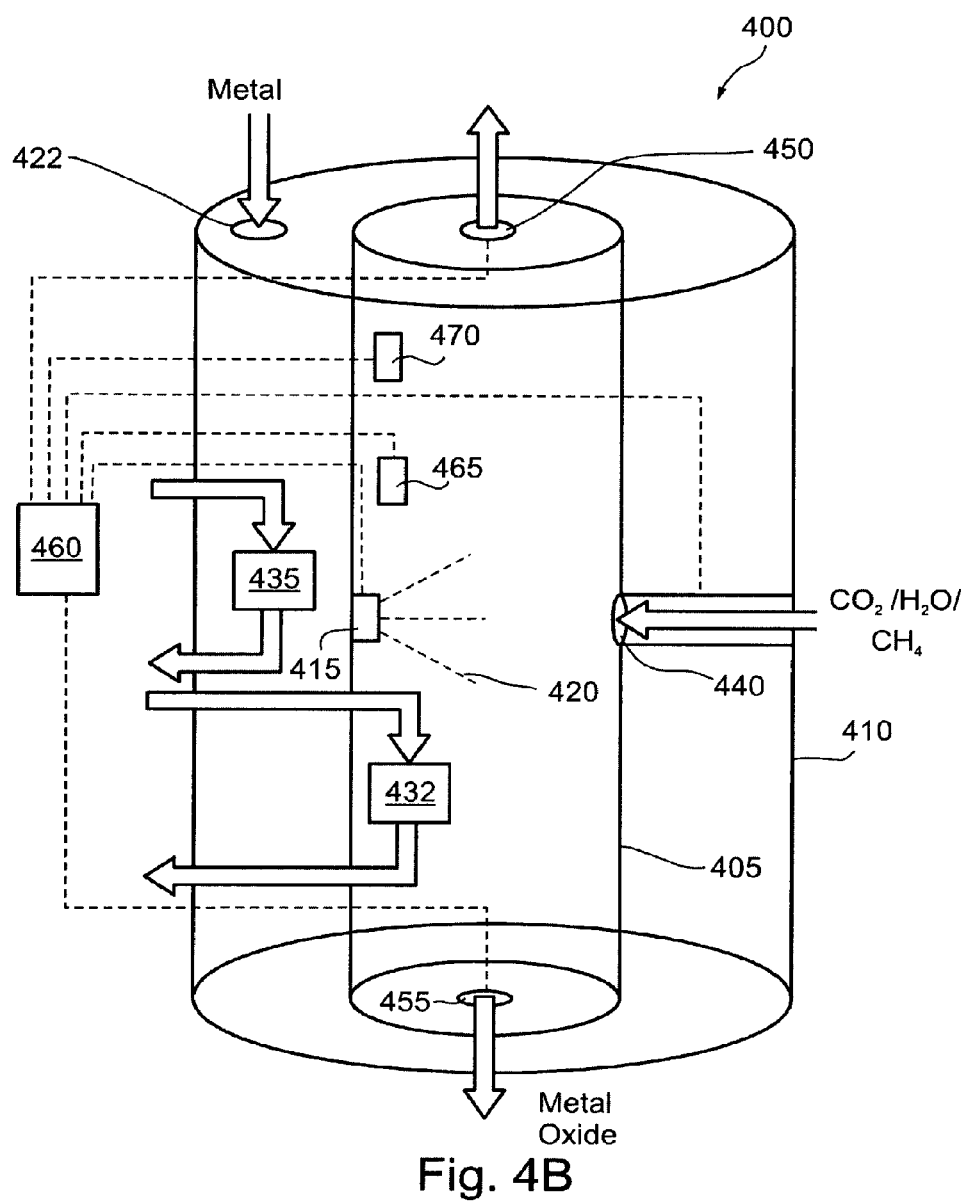

FIGS. 4A and 4B are simplified schematic illustrations of syngas producing units 400 and 400' for oxidizing metals with water to form hydrogen and metal oxide and/or for oxidizing metals with $CO_2$ to form CO and metal oxide. Another suitable syngas producing unit is described in Applicants' patent application WO2006/123330, the disclosure of which is incorporated by reference. Other methods, known in the art for producing syngas from $CO_2$ and water can also be used, in some embodiments of the invention.

Devices 400 and 400' comprise two containers. One container (405) is a reaction chamber, and the other container (410) contains the metal (420) in liquid form.

Reaction chamber 405 comprises a sprinkle or nozzle (415), configured to supply liquid metal 420 from container 410 to the reaction chamber.

Optionally, metal 420 is supplied to container 410 in solid state, for instance, in the form of powder, a rod or a wire, and heated to liquefy and/or to remain at liquid state by heat produced in reaction chamber 405 during operation.

In an embodiment where metal 420 is supplied as a rod or wire, pressure is optionally used to force the metal into the container through inlet 422. Optionally, inlet 422 comprises elastic seals, as described, for instance, in Applicants' patent application No. WO2006/123330, incorporated herein by reference.

Optionally, the pressure used to force the metal into container 405 is utilized for pushing liquid metal 420 into reaction chamber 405. Additionally or alternatively, a pump 425 is used for said pushing.

In FIG. 4A, a heat exchanger 430 is used to transfer the heat from reaction chamber 405 to container 410.

In FIG. 4B, the two containers 405 and 410 are structured in a concentric structure, allowing the absence of a heat exchanger between them.

Optionally, the reaction chamber 405 has in it a heat exchanger 432 for cooling the atmosphere in the reaction chamber, to allow evacuating heat from the reaction chamber as to push forward the exothermic reactions that take place in the reaction chamber.

An external heat exchanger 435 is optionally used for supplying heat from reaction chamber 405 (or metal container 410) to other applications, for instance, for a $CO_2$ separation unit.

Reaction chamber 405 is equipped with at least one inlet 440, configured to inlet at least one of water, carbon dioxide, and methane. Optionally, reaction chamber 405 has one, two, or more additional inlets, each configured to inlet at least one of water, carbon dioxide and methane.

In an exemplary embodiment of the invention, inlet 440 is for inletting methane and carbon dioxide together, optionally, from a source having them together, for instance, natural gas.

In an exemplary embodiment of the invention, inlet 440 is for inletting water and carbon dioxide together, optionally, from a source containing them together, for instance, wet potassium carbonate, which upon heating supplies $CO_2$ and water vapor. Optionally, the pressure in reaction chamber 405 is designed to fit the pressure under which the syngas has to react in the fuel producing unit to give fuel. For instance, if methanol is to be produced at about 50 Atm (5000 kPa), the syngas producing unit is optionally operated at 50 Atm.

Optionally, inlet 440 is configured for simultaneous inletting of water, $CO_2$ and methane.

Reaction chamber 405 also has a syngas outlet 450 and optionally a metal oxide outlet 455. An oxide outlet according to an exemplary embodiment of the invention is described bellow in relation to FIG. 5. In some embodiments, the metal oxide exits together with the syngas, and a separate outlet such as 455 is optionally omitted.

A control system (460) controls the syngas composition by controlling the rate of introduction of the reactants (including metal, and at least one of water, carbon dioxide, and methane) into the reaction chamber (405). Control system 460 optionally also controls syngas outlet 450, and/or oxide outlet 455.

Additionally or alternatively, syngas outlet 450 is controlled by a fuel producing unit (for example unit 150 in FIG. 1) that receives the syngas leaving from the outlet. Optionally, the fuel producing unit communicates with the syngas producing unit through control system 460. Optionally, control system 460 receives data on temperature and pressure inside reaction chamber 405 from temperature sensor 465 and pressure sensor 470. Preferably, device 400 or 400' comprises a plurality of temperature sensors, for sensing temperature at a plurality of locations inside reaction chamber 405.

Ignition of the metal in reaction chamber 405 is obtained, for example, by electric spark, discharge, or a hot filament.

Figure 5:
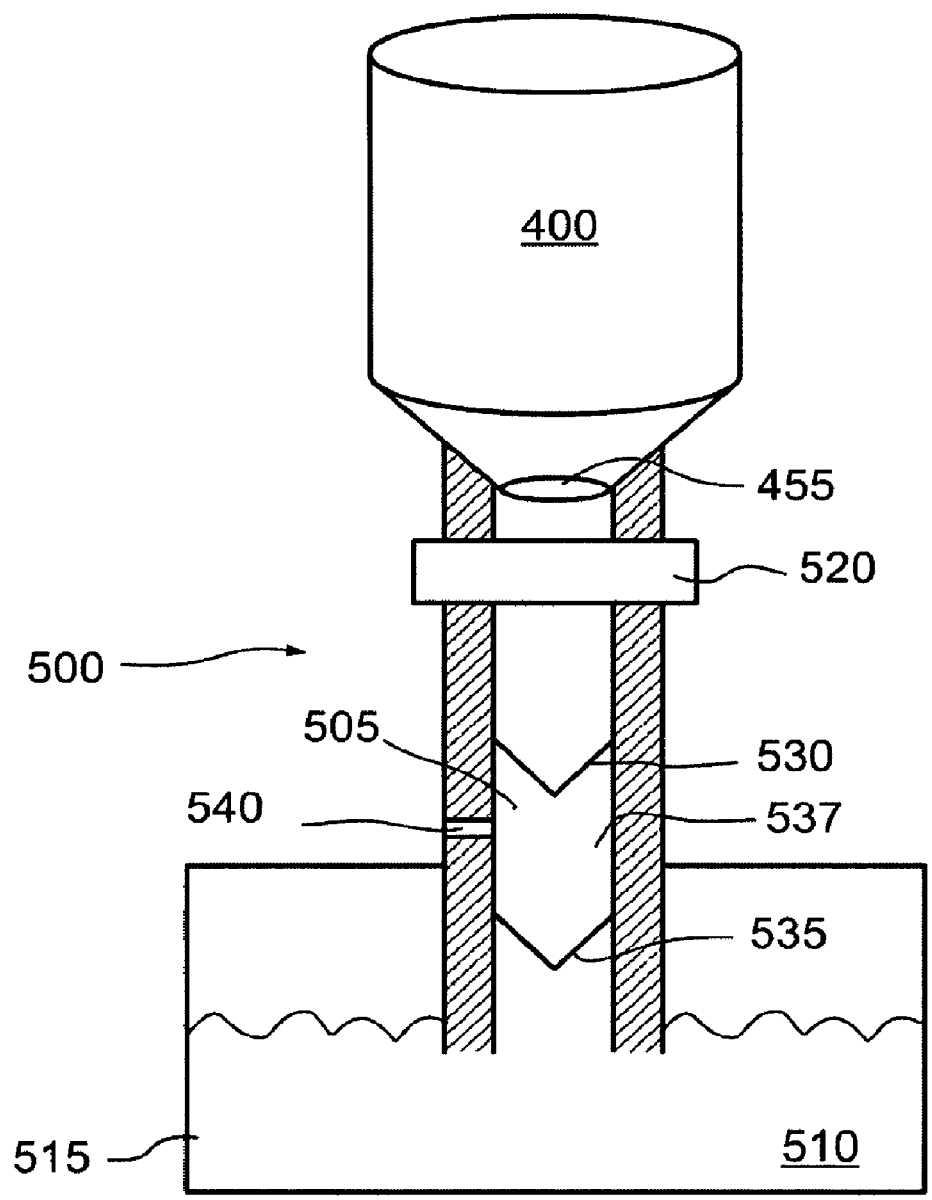
FIG. 5 is a schematic illustration of an oxide removing device, for removing to oxide from a syngas producing unit according to an embodiment of the invention.

FIG. 5 is a schematic illustration of an oxide removing device 500, for removing oxide from a syngas producing unit 400 according to an embodiment of the invention. Details of unit 400 are not provided, except for outlet 455. Optionally, unit 400 has a conical lower surface with the tip being at outlet 455, such that oxide particles formed during operation of unit 400 concentrate by gravity at outlet 455. Smaller or lighter oxide particles, that do not fall down, but rather go up with the syngas stream are not treated by device 500.

Device 500 comprises a conduit 505, optionally leading into an electrolytic bath 510. Conduit 505 has an upper gate valve 530 and a lower gate valve 535, defining between them an intermediate zone (537). An acid inlet 540 is provided for introducing acid into intermediate zone 537. A heat exchanger 520 is positioned as to cool particles going from unit 400 towards conduit 505.

In operation, oxide particles coming into conduit 505 from syngas producing unit 400 are first cooled by heat exchanger 520, and then enter the conduit through upper gate valve 530. Acid, for example sulfuric acid, is entered into conduit 505 through acid inlet 540 to dissolve the oxide particles. Lower gate valve 535 opens to allow the metal oxide particles dissolved in the acid to pour into bath 510. Optionally, the metal oxide is electrolyzed in bath 510.

The pressure in the syngas producing unit 400 is preferably higher than the pressure in the conduit (the latter being optionally atmospheric pressure), to facilitate movement of oxide particles down into conduit 505 and prevent movement of acid up through the conduit.

In an embodiment of the invention, where metal regeneration is not by electrolysis, the use of acid to dissolve the metal oxide and/or the use of an electrolyzer may be omitted. In these embodiments the metal oxide is optionally cooled, and transferred for regeneration by reaction with methane, by heat, or by any other way known in the art per se.

General

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations of these embodiments will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "recycle" and "regenerate" are used in the present description and claims interchangeably.

What is claimed is:

1. A method comprising:
    introducing zinc, water, carbon dioxide, and methane into a reaction chamber, wherein the zinc is liquid,
    reacting water and carbon dioxide with the zinc in the reaction chamber to obtain hydrogen, carbon monoxide, and zinc oxide; and
    regenerating zinc from the zinc oxide in the reaction chamber, by allowing the zinc oxide to react with the methane simultaneously with the reacting of water and carbon dioxide with the zinc to obtain hydrogen, carbon monoxide, and zinc oxide,
    wherein pressure and temperature conditions are selected to carry out the reacting with liquid zinc.

2. The method of claim 1, wherein the method is carried out at substantially stoichiometric ratios of the water, the carbon dioxide and the methane, so as to avoid an excess of reactants.

3. The method of claim 2, wherein the water, the carbon dioxide and the methane are introduced through a single inlet.

4. The method of claim 1, further comprising reacting syngas, comprising the carbon monoxide and the hydrogen, to obtain a fuel.

5. The method of claim 4, further comprising cooling the syngas by a gas turbine using the syngas as a working fluid.

6. The method of claim 4, wherein
the reacting water and carbon dioxide with zinc in the reaction chamber to obtain hydrogen, carbon monoxide, and zinc oxide is carried out at a water to carbon dioxide ratio of substantially 2:1 to achieve resulting carbon monoxide to hydrogen ratio of substantially 1:2, and
the syngas is reacted to fuel at a pressure of substantially 50 atmospheres and temperature of substantially 200° C.

7. The method of claim 1, further comprising separating at least a portion of the carbon dioxide from a gas mixture received from at least one of: landfill gas, natural gas, fermentation gaseous products, and introducing the separated carbon dioxide into the reaction chamber.

8. The method of claim 7, wherein the separating comprises contacting the gas mixture with a solution comprising water and a base to obtain a salt; and heating the salt to release the carbon dioxide.

9. The method of claim 7, wherein carbon dioxide and the methane are separated from at least one of: landfill gas, natural gas, fermentation gaseous products.

10. The method of claim 1, wherein the reaction is carried out under a pressure between ambient and 50 atmospheres and a temperature above 800° C.

* * * * *